United States Patent
Sasson et al.

(10) Patent No.: US 10,228,360 B2
(45) Date of Patent: Mar. 12, 2019

(54) SYSTEM AND METHOD FOR DETERMINING THE QUALITY OF CONCRETE

(71) Applicants: Michael Sasson, Petah Tikva (IL); Ron Zass, Kiryat Tivon (IL)

(72) Inventors: Michael Sasson, Petah Tikva (IL); Ron Zass, Kiryat Tivon (IL)

(73) Assignee: Constru LTD, Tel Aviv (IL)

( * ) Notice: Subject to any disclaimer, the term of this patent is extended or adjusted under 35 U.S.C. 154(b) by 14 days.

(21) Appl. No.: 15/898,627

(22) Filed: Feb. 18, 2018

(65) Prior Publication Data

US 2018/0172662 A1    Jun. 21, 2018

(51) Int. Cl.
  *G06T 7/00*   (2017.01)
  *G01N 33/38*  (2006.01)

(52) U.S. Cl.
  CPC ......... *G01N 33/383* (2013.01); *G06T 7/0004* (2013.01); *G06T 2207/30132* (2013.01)

(58) Field of Classification Search
  CPC ................ G01N 33/383; G06T 7/0004; G06T 2207/30132
  See application file for complete search history.

(56) References Cited

U.S. PATENT DOCUMENTS

| | | | |
|---|---|---|---|
| 6,598,485 B1 * | 7/2003 | Lin | G01N 3/30 73/12.01 |
| 2005/0152432 A1 * | 7/2005 | Hakimuddin | G01N 3/00 374/53 |
| 2013/0034298 A1 * | 2/2013 | Jahanshahi | G06K 9/00624 382/156 |
| 2013/0169794 A1 * | 7/2013 | Shimomura | E01C 23/01 348/128 |
| 2014/0013833 A1 * | 1/2014 | Hosoda | G01N 33/383 73/73 |
| 2014/0249788 A1 * | 9/2014 | Marchand | G06F 17/5009 703/6 |
| 2017/0108456 A1 * | 4/2017 | Alizadeh | C04B 40/0007 |
| 2017/0370898 A1 * | 12/2017 | Radjy | G01N 33/383 |
| 2018/0137612 A1 * | 5/2018 | Li | G06T 7/0004 |

* cited by examiner

*Primary Examiner* — Vincent Rudolph
*Assistant Examiner* — Pinalben Patel

(57) ABSTRACT

System and method for processing images of concrete are provided. Image data captured from a construction site may be obtained. The image data may be analyzed to identify regions of the image data that depict concrete. The image data may be analyzed to determine quality indications associated with concrete depicted in the image data, for example in a region identified above. In some examples, the quality indications may comprise an indication of the durability of the concrete, of the strength of the concrete, and so forth.

20 Claims, 10 Drawing Sheets

SYSTEM AND METHOD FOR DETERMINING THE QUALITY OF CONCRETE

BACKGROUND

Technological Field

The disclosed embodiments generally relate to systems and methods for processing images. More particularly, the disclosed embodiments relate to systems and methods for processing images of concrete.

Background Information

Image sensors are now part of numerous devices, from security systems to mobile phones, and the availability of images and videos produced by those devices is increasing.

SUMMARY

In some embodiments, systems and methods for processing images of concrete are provided.

In some embodiments, image data captured from a construction site may be obtained. The image data may be analyzed to identify regions of the image data that depicts concrete. The image data may be analyzed to determine quality indications associated with concrete depicted in the image data, for example in a region identified above. In some examples, the quality indications may comprise an indication of the durability of the concrete, of the strength of the concrete, and so forth. In some examples, the quality indications may comprise an estimate of a compressive strength test conducted after a selected curing time, of a result of a water permeability test, of a result of a rapid chloride ion penetration test, of a result of a water absorption test, of a result of an initial surface absorption test, and so forth. In some examples, the quality indications may be based on a condition of the concrete, such as segregation of the concrete, discoloration of the concrete, scaling of the concrete, crazing of the concrete, cracking of the concrete, curling of the concrete, and so forth. In some examples, the quality indications may be compared to selected thresholds, to quality indications associated with other regions of concrete, and so forth.

DESCRIPTION

Figure 1A:
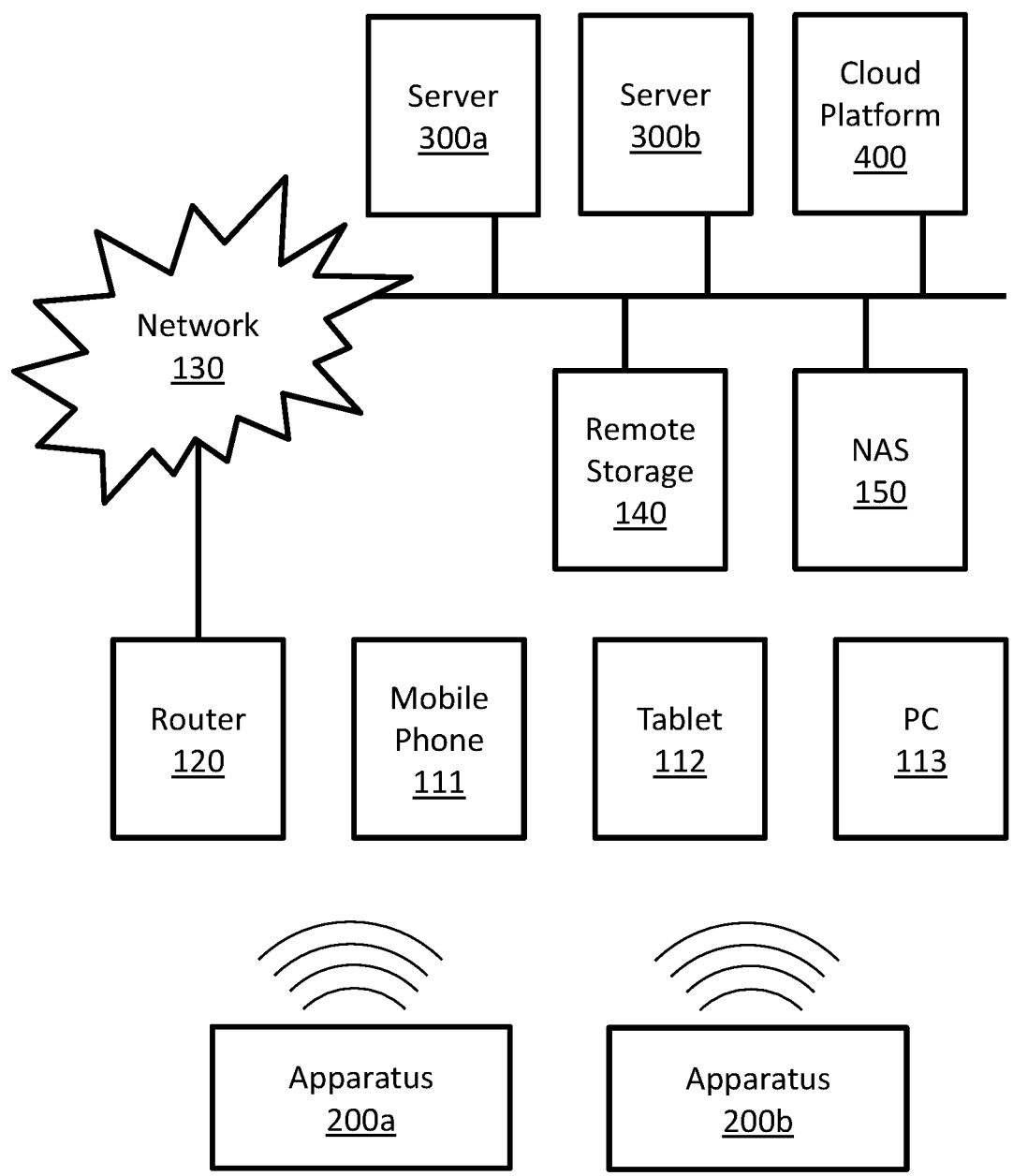
FIGS. 1A and 1B are block diagrams illustrating some possible implementations of a communicating system.

Unless specifically stated otherwise, as apparent from the following discussions, it is appreciated that throughout the specification discussions utilizing terms such as "processing", "calculating", "computing", "determining", "generating", "setting", "configuring", "selecting", "defining", "applying", "obtaining", "monitoring", "providing", "identifying", "segmenting", "classifying", "analyzing", "associating", "extracting", "storing", "receiving", "transmitting", or the like, include action and/or processes of a computer that manipulate and/or transform data into other data, said data represented as physical quantities, for example such as electronic quantities, and/or said data representing the physical objects. The terms "computer", "processor", "controller", "processing unit", "computing unit", and "processing module" should be expansively construed to cover any kind of electronic device, component or unit with data processing capabilities, including, by way of non-limiting example, a personal computer, a wearable computer, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) may be included in at least one embodiment of the presently disclosed subject matter. Thus the appearance of the phrase "one case", "some cases", "other cases" or variants thereof does not necessarily refer to the same embodiment(s). As used herein, the term "and/or" includes any and all combinations of one or more of the associated listed items.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

The term "image sensor" is recognized by those skilled in the art and refers to any device configured to capture images, a sequence of images, videos, and so forth. This includes sensors that convert optical input into images, where optical input can be visible light (like in a camera), radio waves, microwaves, terahertz waves, ultraviolet light, infrared light, x-rays, gamma rays, and/or any other light spectrum. This also includes both 2D and 3D sensors. Examples of image sensor technologies may include: CCD, CMOS, NMOS, and so forth. 3D sensors may be implemented using different technologies, including: stereo camera, active stereo camera, time of flight camera, structured light camera, radar, range image camera, and so forth.

The term "compressive strength test" is recognized by those skilled in the art and refers to a test that mechanically measure the maximal amount of compressive load a material, such as a body or a cube of concrete, can bear before fracturing.

The term "water permeability test" is recognized by those skilled in the art and refers to a test of a body or a cube of concrete that measures the depth of penetration of water maintained at predetermined pressures for a predetermined time intervals.

The term "rapid chloride ion penetration test" is recognized by those skilled in the art and refers to a test that measures the ability of concrete to resist chloride ion penetration.

The term "water absorption test" is recognized by those skilled in the art and refers to a test of concrete specimens that, after drying the specimens, emerges the specimens in water at predetermined temperature and/or pressure for predetermined time intervals, and measures the weight of water absorbed by the specimens.

The term "initial surface absorption test" is recognized by those skilled in the art and refers to a test that measures the flow of water per concrete surface area when subjected to a constant water head.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

It should be noted that some examples of the presently disclosed subject matter are not limited in application to the details of construction and the arrangement of the components set forth in the following description or illustrated in the drawings. The invention can be capable of other embodiments or of being practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

FIG. 1A is a block diagram illustrating a possible implementation of a communicating system. In this example, apparatuses 200a and 200b may communicate with server 300a, with server 300b, with cloud platform 400, with each other, and so forth. Possible implementations of apparatuses 200a and 200b may include apparatus 200 as described in FIGS. 2A and 2B. Possible implementations of servers 300a and 300b may include server 300 as described in FIG. 3. Some possible implementations of cloud platform 400 are described in FIGS. 4A, 4B and 5. In this example apparatuses 200a and 200b may communicate directly with mobile phone 111, tablet 112, and personal computer (PC) 113. Apparatuses 200a and 200b may communicate with local router 120 directly, and/or through at least one of mobile phone 111, tablet 112, and personal computer (PC) 113. In this example, local router 120 may be connected with a communication network 130. Examples of communication network 130 may include the Internet, phone networks, cellular networks, satellite communication networks, private communication networks, virtual private networks (VPN), and so forth. Apparatuses 200a and 200b may connect to communication network 130 through local router 120 and/or directly. Apparatuses 200a and 200b may communicate with other devices, such as servers 300a, server 300b, cloud platform 400, remote storage 140 and network attached storage (NAS) 150, through communication network 130 and/or directly.

Figure 1B:
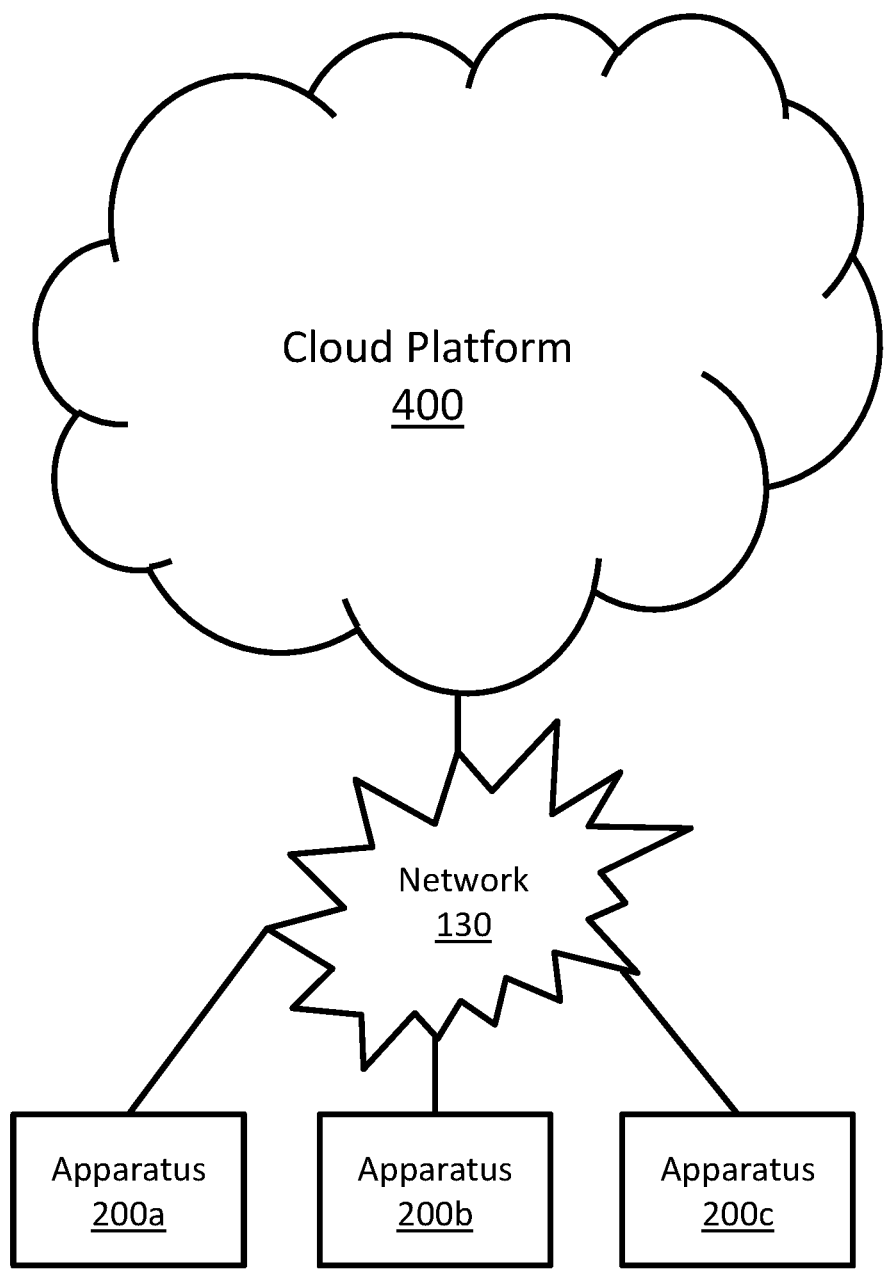

FIG. 1B is a block diagram illustrating a possible implementation of a communicating system. In this example, apparatuses 200a, 200b and 200c may communicate with cloud platform 400 and/or with each other through communication network 130. Possible implementations of apparatuses 200a, 200b and 200c may include apparatus 200 as described in FIGS. 2A and 2B. Some possible implementations of cloud platform 400 are described in FIGS. 4A, 4B and 5.

FIGS. 1A and 1B illustrate some possible implementations of a communication system. In some embodiments, other communication systems that enable communication between apparatus 200 and server 300 may be used. In some embodiments, other communication systems that enable communication between apparatus 200 and cloud platform 400 may be used. In some embodiments, other communication systems that enable communication among a plurality of apparatuses 200 may be used.

Figure 2A:
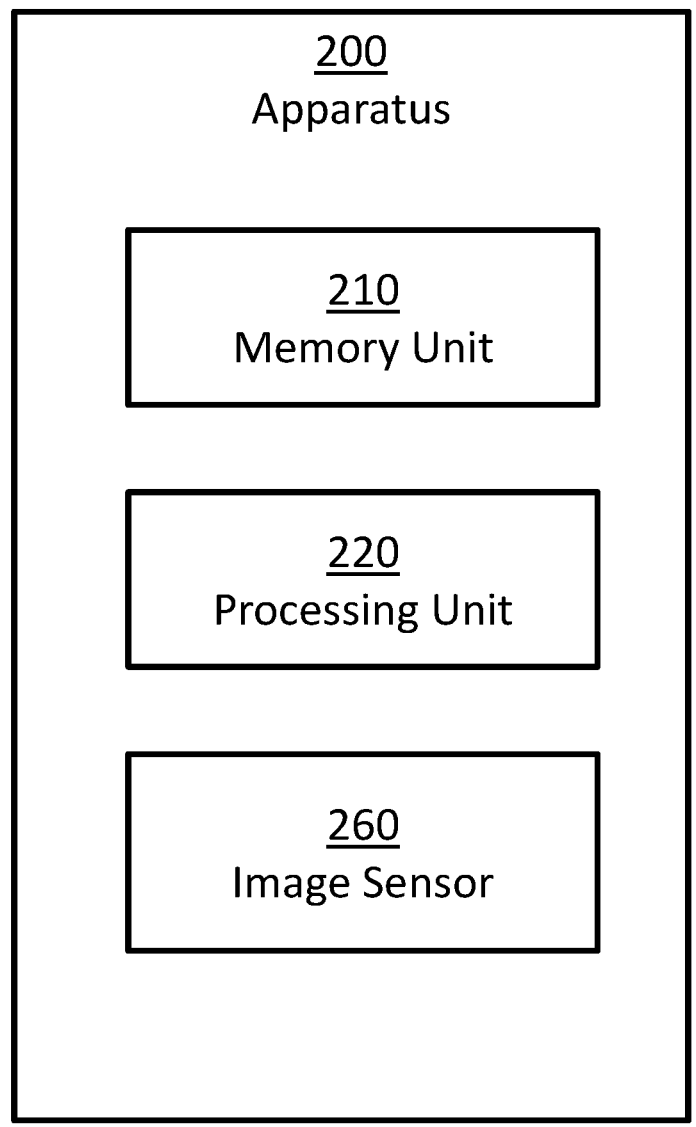
FIGS. 2A and 2B are block diagrams illustrating some possible implementations of an apparatus.

FIG. 2A is a block diagram illustrating a possible implementation of apparatus 200. In this example, apparatus 200 may comprise: one or more memory units 210, one or more processing units 220, and one or more image sensors 260. In some implementations, apparatus 200 may comprise additional components, while some components listed above may be excluded.

Figure 2B:
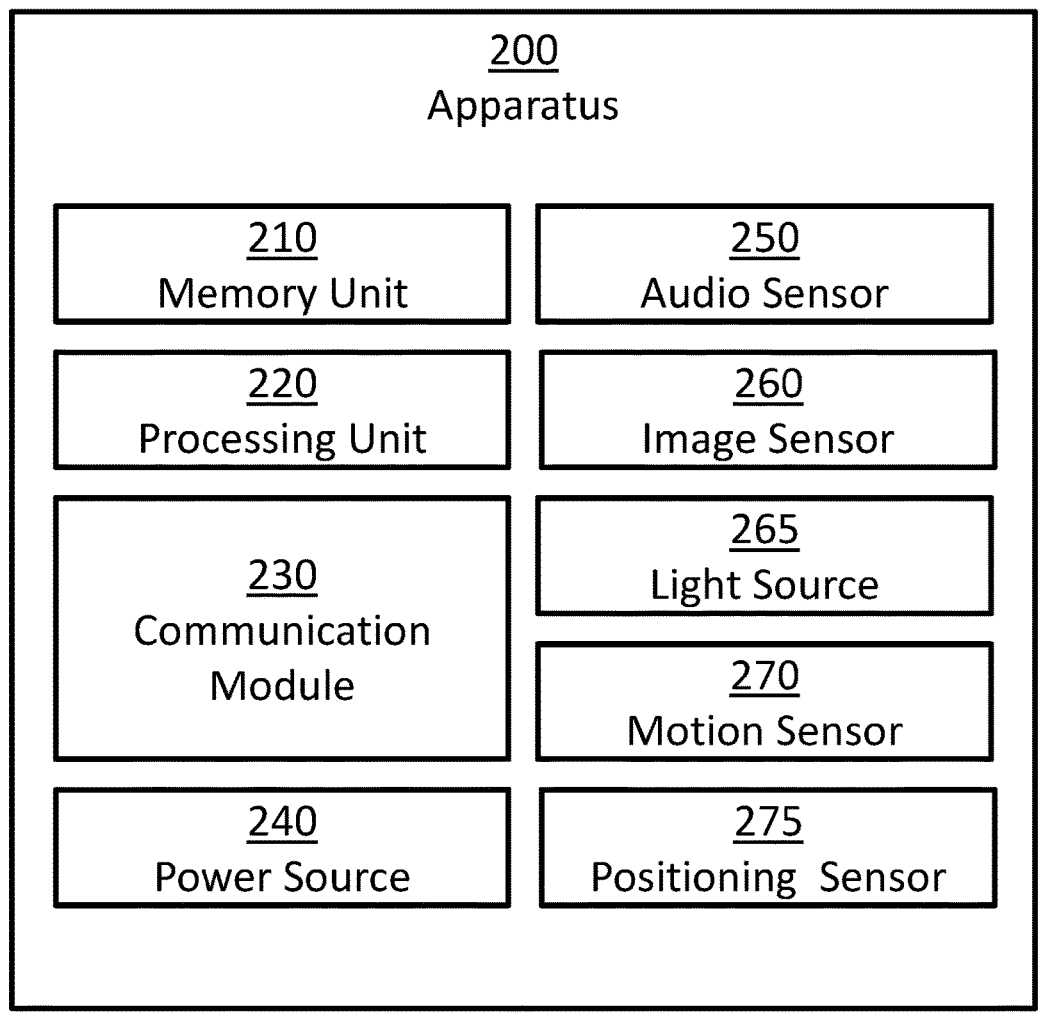

FIG. 2B is a block diagram illustrating a possible implementation of apparatus 200. In this example, apparatus 200 may comprise: one or more memory units 210, one or more processing units 220, one or more communication modules 230, one or more power sources 240, one or more audio sensors 250, one or more image sensors 260, one or more light sources 265, one or more motion sensors 270, and one or more positioning sensors 275. In some implementations, apparatus 200 may comprise additional components, while some components listed above may be excluded. For example, in some implementations apparatus 200 may also comprise at least one of the following: one or more barometers; one or more user input devices; one or more output devices; and so forth. In another example, in some implementations at least one of the following may be excluded from apparatus 200: memory units 210, communication modules 230, power sources 240, audio sensors 250, image sensors 260, light sources 265, motion sensors 270, and positioning sensors 275.

In some embodiments, one or more power sources 240 may be configured to: power apparatus 200; power server 300; power cloud platform 400; and/or power computational node 500. Possible implementation examples of power sources 240 may include: one or more electric batteries; one or more capacitors; one or more connections to external power sources; one or more power converters; any combination of the above; and so forth.

In some embodiments, the one or more processing units 220 may be configured to execute software programs. For example, processing units 220 may be configured to execute software programs stored on the memory units 210. In some cases, the executed software programs may store information in memory units 210. In some cases, the executed software programs may retrieve information from the memory units 210. Possible implementation examples of the processing units 220 may include: one or more single core processors; one or more multicore processors; one or more controllers; one or more application processors; one or more system on a chip processors; one or more central processing units; one or more graphical processing units; one or more neural processing units; any combination of the above; and so forth.

In some embodiments, the one or more communication modules 230 may be configured to receive and transmit information. For example, control signals may be transmitted and/or received through communication modules 230. In another example, information received though communication modules 230 may be stored in memory units 210. In an additional example, information retrieved from memory units 210 may be transmitted using communication modules 230. In another example, input data may be transmitted and/or received using communication modules 230. Examples of such input data may include: input data inputted by a user using user input devices; information captured using one or more sensors; and so forth. Examples of such sensors may include: audio sensors 250; image sensors 260; motion sensors 270; positioning sensors 275; chemical sensors; temperature sensors; barometers; and so forth.

In some embodiments, the one or more audio sensors 250 may be configured to capture audio by converting sounds to digital information. Some examples of audio sensors 250 may include: microphones, unidirectional microphones, bidirectional microphones, cardioid microphones, omnidirectional microphones, onboard microphones, wired microphones, wireless microphones, any combination of the above, and so forth. In some examples, the captured audio may be stored in memory units 210. In some additional examples, the captured audio may be transmitted using communication modules 230, for example to other computerized devices, such as server 300, cloud platform 400, computational node 500, and so forth. In some examples, processing units 220 may control the above processes. For example, processing units 220 may control at least one of: capturing of the audio; storing the captured audio; transmitting of the captured audio; and so forth. In some cases, the captured audio may be processed by processing units 220. For example, the captured audio may be compressed by processing units 220; possibly followed: by storing the compressed captured audio in memory units 210; by transmitted the compressed captured audio using communication modules 230; and so forth. In another example, the captured audio may be processed using speech recognition algorithms. In another example, the captured audio may be processed using speaker recognition algorithms.

In some embodiments, the one or more image sensors 260 may be configured to capture visual information by converting light to: images; sequence of images; videos; 3D images; sequence of 3D images; 3D videos; and so forth. In some examples, the captured visual information may be stored in memory units 210. In some additional examples, the captured visual information may be transmitted using communication modules 230, for example to other computerized devices, such as server 300, cloud platform 400, computational node 500, and so forth. In some examples, processing units 220 may control the above processes. For example, processing units 220 may control at least one of: capturing of the visual information; storing the captured visual information; transmitting of the captured visual information; and so forth. In some cases, the captured visual information may be processed by processing units 220. For example, the captured visual information may be compressed by processing units 220; possibly followed: by storing the compressed captured visual information in memory units 210; by transmitted the compressed captured visual information using communication modules 230; and so forth. In another example, the captured visual information may be processed in order to: detect objects, detect events, detect action, detect face, detect people, recognize person, and so forth.

In some embodiments, the one or more light sources 265 may be configured to emit light, for example in order to enable better image capturing by image sensors 260. In some examples, the emission of light may be coordinated with the capturing operation of image sensors 260. In some examples, the emission of light may be continuous. In some examples, the emission of light may be performed at selected times. The emitted light may be visible light, infrared light, x-rays, gamma rays, and/or in any other light spectrum. In some examples, image sensors 260 may capture light emitted by light sources 265, for example in order to capture 3D images and/or 3D videos using active stereo method.

In some embodiments, the one or more motion sensors 270 may be configured to perform at least one of the following: detect motion of objects in the environment of apparatus 200; measure the velocity of objects in the environment of apparatus 200; measure the acceleration of objects in the environment of apparatus 200; detect motion of apparatus 200; measure the velocity of apparatus 200; measure the acceleration of apparatus 200; and so forth. In some implementations, the one or more motion sensors 270 may comprise one or more accelerometers configured to detect changes in proper acceleration and/or to measure proper acceleration of apparatus 200. In some implementations, the one or more motion sensors 270 may comprise one or more gyroscopes configured to detect changes in the orientation of apparatus 200 and/or to measure information related to the orientation of apparatus 200. In some implementations, motion sensors 270 may be implemented using image sensors 260, for example by analyzing images captured by image sensors 260 to perform at least one of the following tasks: track objects in the environment of apparatus 200; detect moving objects in the environment of apparatus 200; measure the velocity of objects in the environment of apparatus 200; measure the acceleration of objects in the environment of apparatus 200; measure the velocity of apparatus 200, for example by calculating the egomotion of image sensors 260; measure the acceleration of apparatus 200, for example by calculating the egomotion of image sensors 260; and so forth. In some implementations, motion sensors 270 may be implemented using image sensors 260 and light sources 265, for example by implementing a LIDAR using image sensors 260 and light sources 265. In some implementations, motion sensors 270 may be implemented using one or more RADARs. In some examples, information captured using motion sensors 270: may be stored in memory units 210, may be processed by processing units 220, may be transmitted and/or received using communication modules 230, and so forth.

In some embodiments, the one or more positioning sensors 275 may be configured to obtain positioning information of apparatus 200, to detect changes in the position of apparatus 200, and/or to measure the position of apparatus 200. In some examples, positioning sensors 275 may be implemented using one of the following technologies:

Global Positioning System (GPS), GLObal NAvigation Satellite System (GLONASS), Galileo global navigation system, BeiDou navigation system, other Global Navigation Satellite Systems (GNSS), Indian Regional Navigation Satellite System (IRNSS), Local Positioning Systems (LPS), Real-Time Location Systems (RTLS), Indoor Positioning System (IPS), Wi-Fi based positioning systems, cellular triangulation, and so forth. In some examples, information captured using positioning sensors 275 may be stored in memory units 210, may be processed by processing units 220, may be transmitted and/or received using communication modules 230, and so forth.

In some embodiments, the one or more chemical sensors may be configured to perform at least one of the following: measure chemical properties in the environment of apparatus 200; measure changes in the chemical properties in the environment of apparatus 200; detect the present of chemicals in the environment of apparatus 200; measure the concentration of chemicals in the environment of apparatus 200. Examples of such chemical properties may include: pH level, toxicity, temperature, and so forth. Examples of such chemicals may include: electrolytes, particular enzymes, particular hormones, particular proteins, smoke, carbon dioxide, carbon monoxide, oxygen, ozone, hydrogen, hydrogen sulfide, and so forth. In some examples, information captured using chemical sensors may be stored in memory units 210, may be processed by processing units 220, may be transmitted and/or received using communication modules 230, and so forth.

In some embodiments, the one or more temperature sensors may be configured to detect changes in the temperature of the environment of apparatus 200 and/or to measure the temperature of the environment of apparatus 200. In some examples, information captured using temperature sensors may be stored in memory units 210, may be processed by processing units 220, may be transmitted and/or received using communication modules 230, and so forth.

In some embodiments, the one or more barometers may be configured to detect changes in the atmospheric pressure in the environment of apparatus 200 and/or to measure the atmospheric pressure in the environment of apparatus 200. In some examples, information captured using the barometers may be stored in memory units 210, may be processed by processing units 220, may be transmitted and/or received using communication modules 230, and so forth.

In some embodiments, the one or more user input devices may be configured to allow one or more users to input information. In some examples, user input devices may comprise at least one of the following: a keyboard, a mouse, a touch pad, a touch screen, a joystick, a microphone, an image sensor, and so forth. In some examples, the user input may be in the form of at least one of: text, sounds, speech, hand gestures, body gestures, tactile information, and so forth. In some examples, the user input may be stored in memory units 210, may be processed by processing units 220, may be transmitted and/or received using communication modules 230, and so forth.

In some embodiments, the one or more user output devices may be configured to provide output information to one or more users. In some examples, such output information may comprise of at least one of: notifications, feedbacks, reports, and so forth. In some examples, user output devices may comprise at least one of: one or more audio output devices; one or more textual output devices; one or more visual output devices; one or more tactile output devices; and so forth. In some examples, the one or more audio output devices may be configured to output audio to a user, for example through: a headset, a set of speakers, and so forth. In some examples, the one or more visual output devices may be configured to output visual information to a user, for example through: a display screen, an augmented reality display system, a printer, a LED indicator, and so forth. In some examples, the one or more tactile output devices may be configured to output tactile feedbacks to a user, for example through vibrations, through motions, by applying forces, and so forth. In some examples, the output may be provided: in real time, offline, automatically, upon request, and so forth. In some examples, the output information may be read from memory units 210, may be provided by a software executed by processing units 220, may be transmitted and/or received using communication modules 230, and so forth.

Figure 3:
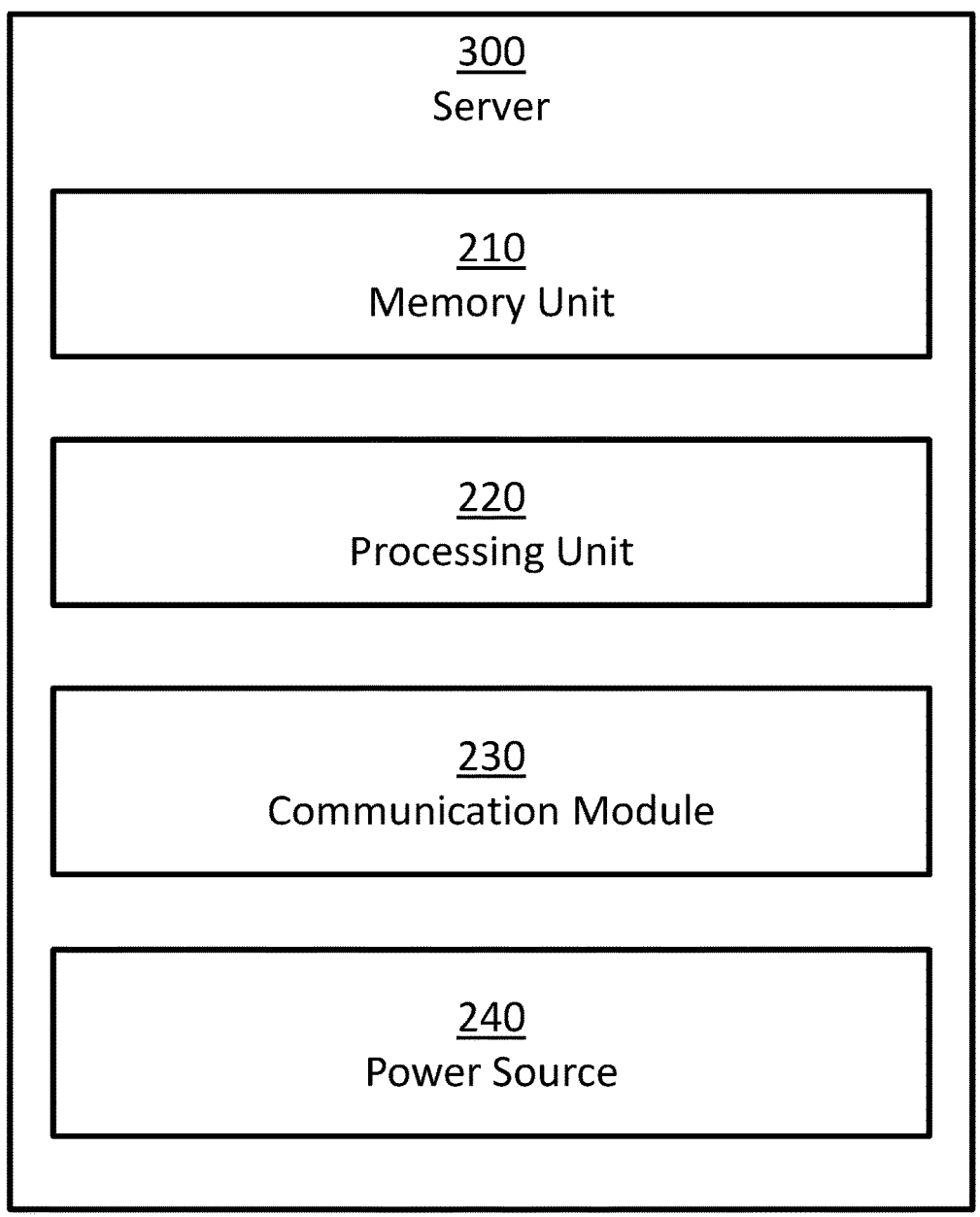
FIG. 3 is a block diagram illustrating a possible implementation of a server.

FIG. 3 is a block diagram illustrating a possible implementation of server 300. In this example, server 300 may comprise: one or more memory units 210, one or more processing units 220, one or more communication modules 230, and one or more power sources 240. In some implementations, server 300 may comprise additional components, while some components listed above may be excluded. For example, in some implementations server 300 may also comprise at least one of the following: one or more user input devices; one or more output devices; and so forth. In another example, in some implementations at least one of the following may be excluded from server 300: memory units 210, communication modules 230, and power sources 240.

Figure 4A:
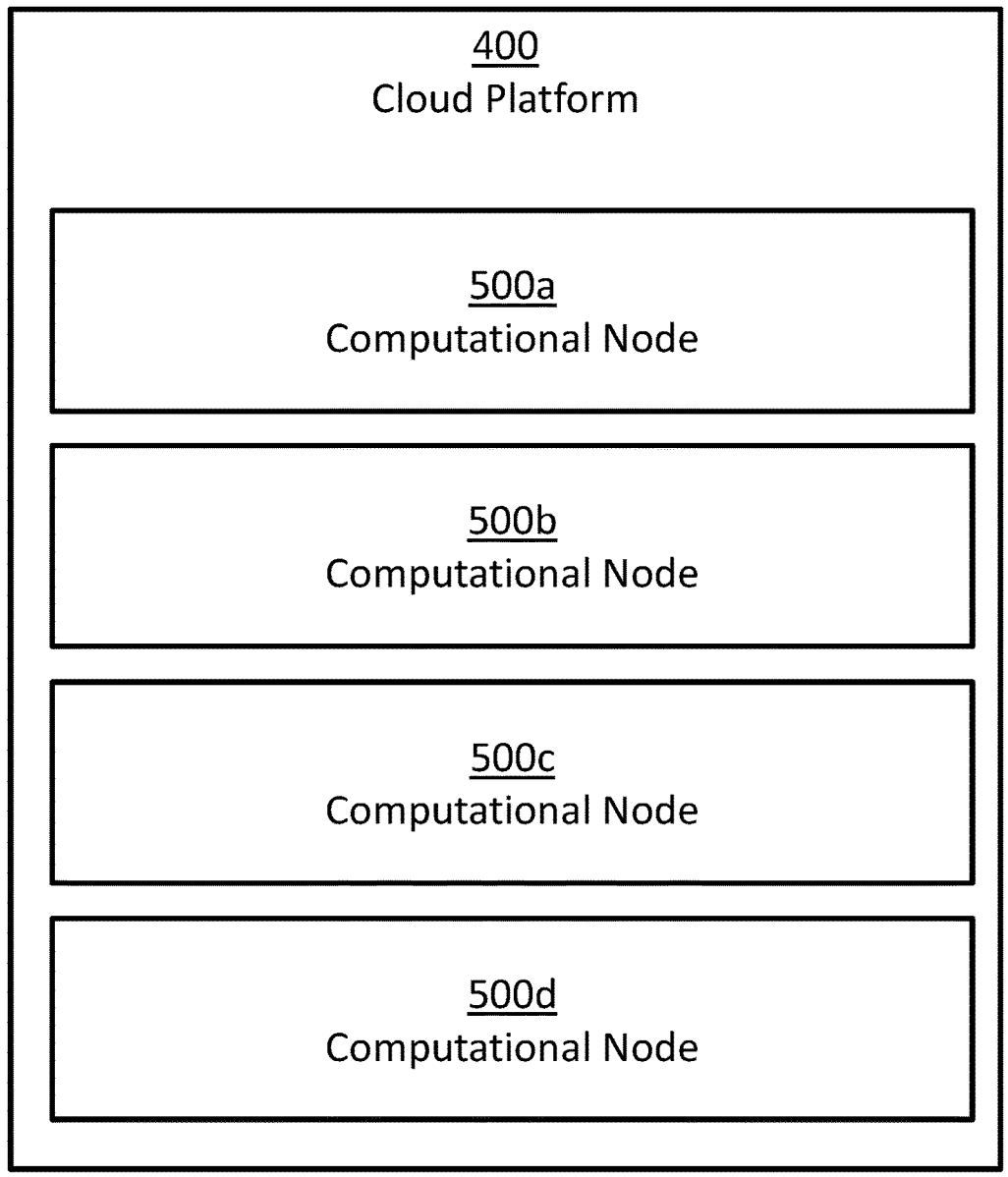
FIGS. 4A and 4B are block diagrams illustrating some possible implementations of a cloud platform.

FIG. 4A is a block diagram illustrating a possible implementation of cloud platform 400. In this example, cloud platform 400 may comprise computational node 500*a*, computational node 500*b*, computational node 500*c* and computational node 500*d*. In some examples, a possible implementation of computational nodes 500*a*, 500*b*, 500*c* and 500*d* may comprise server 300 as described in FIG. 3. In some examples, a possible implementation of computational nodes 500*a*, 500*b*, 500*c* and 500*d* may comprise computational node 500 as described in FIG. 5.

Figure 4B:
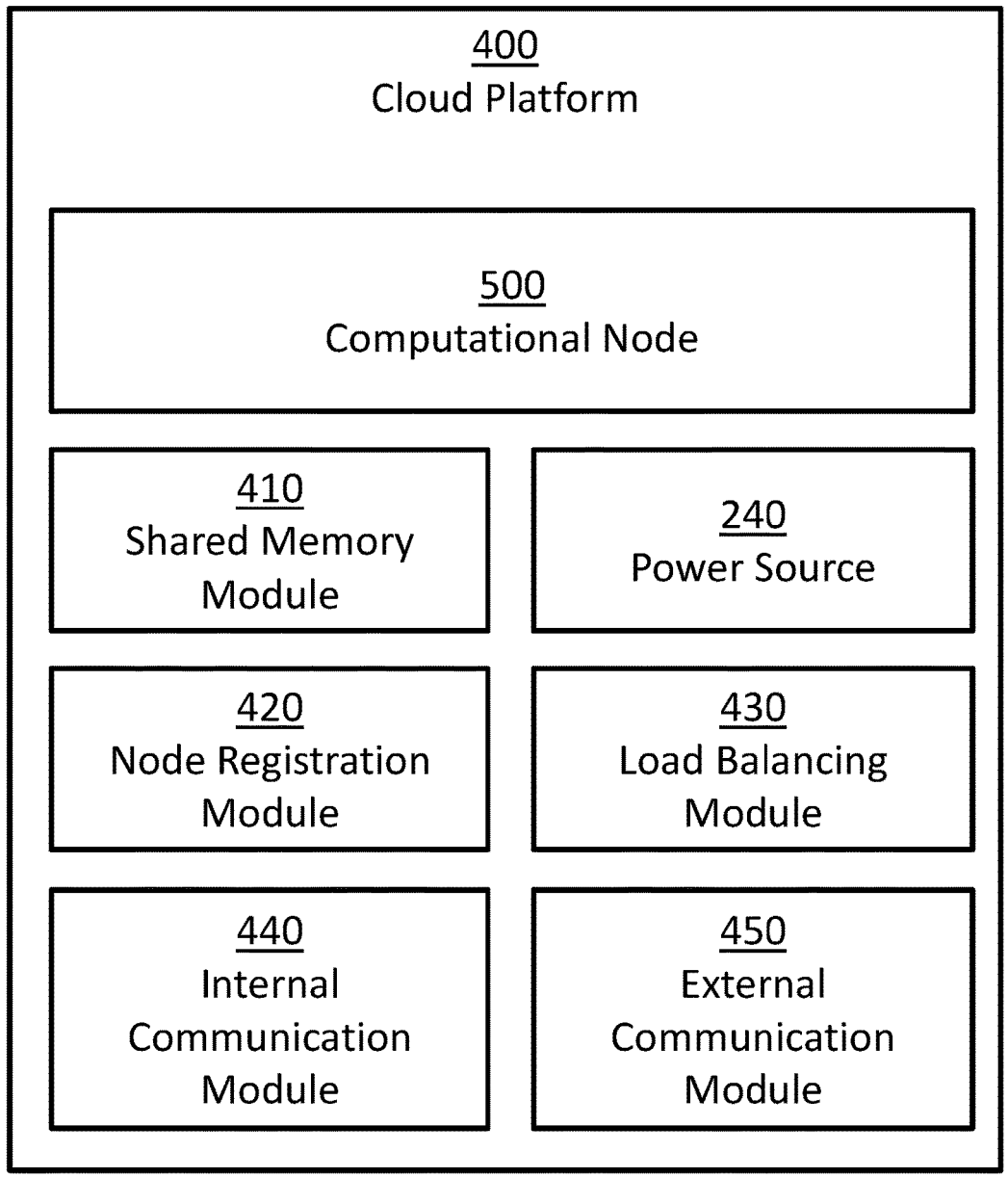

FIG. 4B is a block diagram illustrating a possible implementation of cloud platform 400. In this example, cloud platform 400 may comprise: one or more computational nodes 500, one or more shared memory modules 410, one or more power sources 240, one or more node registration modules 420, one or more load balancing modules 430, one or more internal communication modules 440, and one or more external communication modules 450. In some implementations, cloud platform 400 may comprise additional components, while some components listed above may be excluded. For example, in some implementations cloud platform 400 may also comprise at least one of the following: one or more user input devices; one or more output devices; and so forth. In another example, in some implementations at least one of the following may be excluded from cloud platform 400: shared memory modules 410, power sources 240, node registration modules 420, load balancing modules 430, internal communication modules 440, and external communication modules 450.

Figure 5:
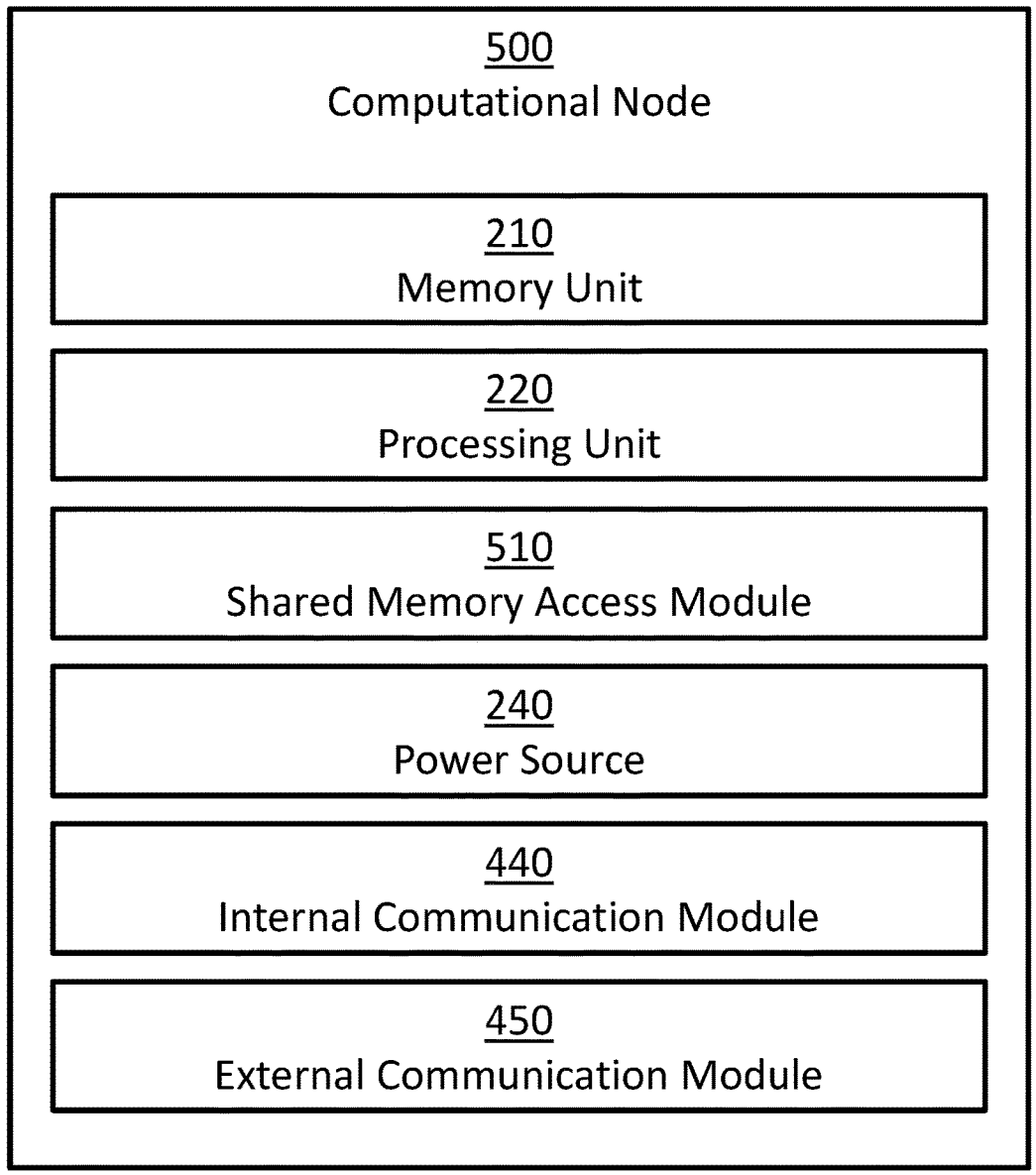
FIG. 5 is a block diagram illustrating a possible implementation of a computational node.

FIG. 5 is a block diagram illustrating a possible implementation of computational node 500. In this example, computational node 500 may comprise: one or more memory units 210, one or more processing units 220, one or more shared memory access modules 510, one or more power sources 240, one or more internal communication modules 440, and one or more external communication modules 450. In some implementations, computational node 500 may comprise additional components, while some components listed above may be excluded. For example, in some implementations computational node 500 may also comprise at least one of the following: one or more user input devices; one or more output devices; and so forth. In another example, in some implementations at least one of the following may be excluded from computational node 500: memory units 210, shared memory access modules 510, power sources 240, internal communication modules 440, and external communication modules 450.

In some embodiments, internal communication modules 440 and external communication modules 450 may be implemented as a combined communication module, such as communication modules 230. In some embodiments, one possible implementation of cloud platform 400 may comprise server 300. In some embodiments, one possible implementation of computational node 500 may comprise server 300. In some embodiments, one possible implementation of shared memory access modules 510 may comprise using internal communication modules 440 to send information to shared memory modules 410 and/or receive information from shared memory modules 410. In some embodiments, node registration modules 420 and load balancing modules 430 may be implemented as a combined module.

In some embodiments, the one or more shared memory modules 410 may be accessed by more than one computational node. Therefore, shared memory modules 410 may allow information sharing among two or more computational nodes 500. In some embodiments, the one or more shared memory access modules 510 may be configured to enable access of computational nodes 500 and/or the one or more processing units 220 of computational nodes 500 to shared memory modules 410. In some examples, computational nodes 500 and/or the one or more processing units 220 of computational nodes 500, may access shared memory modules 410, for example using shared memory access modules 510, in order to perform at least one of: executing software programs stored on shared memory modules 410, store information in shared memory modules 410, retrieve information from the shared memory modules 410.

In some embodiments, the one or more node registration modules 420 may be configured to track the availability of the computational nodes 500. In some examples, node registration modules 420 may be implemented as: a software program, such as a software program executed by one or more of the computational nodes 500; a hardware solution; a combined software and hardware solution; and so forth. In some implementations, node registration modules 420 may communicate with computational nodes 500, for example using internal communication modules 440. In some examples, computational nodes 500 may notify node registration modules 420 of their status, for example by sending messages: at computational node 500 startup; at computational node 500 shutdown; at constant intervals; at selected times; in response to queries received from node registration modules 420; and so forth. In some examples, node registration modules 420 may query about computational nodes 500 status, for example by sending messages: at node registration module 420 startup; at constant intervals; at selected times; and so forth.

In some embodiments, the one or more load balancing modules 430 may be configured to divide the work load among computational nodes 500. In some examples, load balancing modules 430 may be implemented as: a software program, such as a software program executed by one or more of the computational nodes 500; a hardware solution; a combined software and hardware solution; and so forth. In some implementations, load balancing modules 430 may interact with node registration modules 420 in order to obtain information regarding the availability of the computational nodes 500. In some implementations, load balancing modules 430 may communicate with computational nodes 500, for example using internal communication modules 440. In some examples, computational nodes 500 may notify load balancing modules 430 of their status, for example by sending messages: at computational node 500 startup; at computational node 500 shutdown; at constant intervals; at selected times; in response to queries received from load balancing modules 430; and so forth. In some examples, load balancing modules 430 may query about computational nodes 500 status, for example by sending messages: at load balancing module 430 startup; at constant intervals; at selected times; and so forth.

In some embodiments, the one or more internal communication modules 440 may be configured to receive information from one or more components of cloud platform 400, and/or to transmit information to one or more components of cloud platform 400. For example, control signals and/or synchronization signals may be sent and/or received through internal communication modules 440. In another example, input information for computer programs, output information of computer programs, and/or intermediate information of computer programs, may be sent and/or received through internal communication modules 440. In another example, information received though internal communication modules 440 may be stored in memory units 210, in shared memory units 410, and so forth. In an additional example, information retrieved from memory units 210 and/or shared memory units 410 may be transmitted using internal communication modules 440. In another example, input data may be transmitted and/or received using internal communication modules 440. Examples of such input data may include input data inputted by a user using user input devices.

In some embodiments, the one or more external communication modules 450 may be configured to receive and/or to transmit information. For example, control signals may be sent and/or received through external communication modules 450. In another example, information received though external communication modules 450 may be stored in memory units 210, in shared memory units 410, and so forth. In an additional example, information retrieved from memory units 210 and/or shared memory units 410 may be transmitted using external communication modules 450. In another example, input data may be transmitted and/or received using external communication modules 450. Examples of such input data may include: input data inputted by a user using user input devices; information captured from the environment of apparatus 200 using one or more sensors; and so forth. Examples of such sensors may include: audio sensors 250; image sensors 260; motion sensors 270; positioning sensors 275; chemical sensors; temperature sensors; barometers; and so forth.

Figure 6:
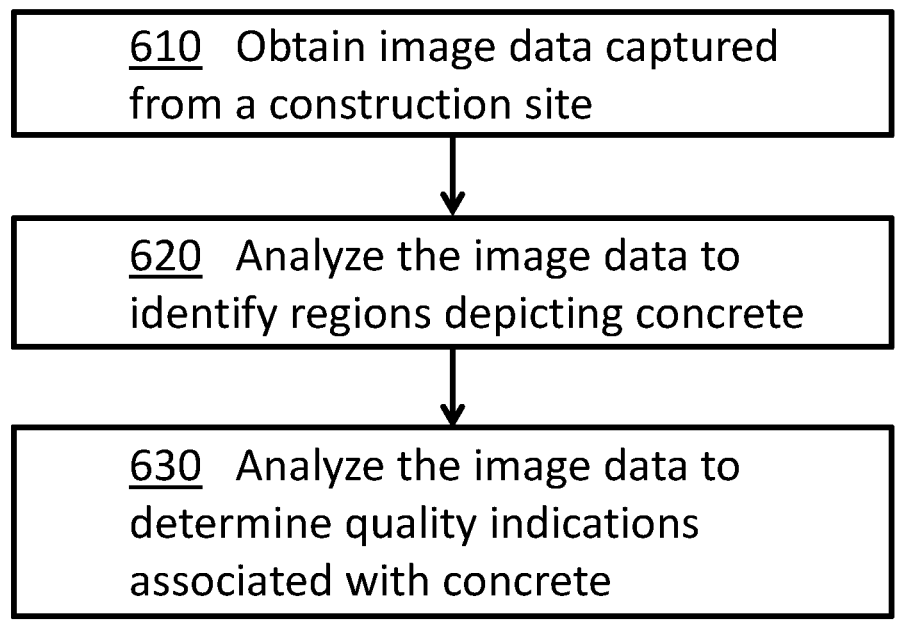
FIG. 6 illustrates an example of a process for processing images of concrete.

FIG. 6 illustrates an example of process 600 for processing images of concrete. In some examples, process 600, as well as all individual steps therein, may be performed by various aspects of: apparatus 200; server 300; cloud platform 400; computational node 500; and so forth. For example, process 600 may be performed by processing units 220, executing software instructions stored within memory units 210 and/or within shared memory modules 410. In this example, process 600 may comprise: obtaining image data captured from a construction site (Step 610); analyzing the image data to identify regions depicting concrete (Step 620); and analyzing the image data to determine quality indications associated with concrete (Step 630). In some implementations, process 600 may comprise one or more additional steps, while some of the steps listed above may be modified or excluded. For example, Step 620 may be excluded from process 600. In some implementations, one or more steps illustrated in FIG. 6 may be executed in a different order and/or one or more groups of steps may be executed simultaneously and vice versa. For example: Step 620 may be executed after and/or simultaneously with Step 610; Step 630 may be executed after and/or simultaneously with Step 610; Step 630 may be executed before, after and/or simultaneously with Step 620; and so forth. Examples of possible execution manners of process 600 may include: continuous execution, returning to the beginning of the process once the process normal execution ends; periodically execution, executing the process at selected times; execution upon the detection of a trigger, where examples of such trigger may include trigger from a user, trigger from another process, etc.; any combination of the above; and so forth.

In some embodiments, obtaining image data captured from a construction site (Step 610) may comprise obtaining image data captured using one or more image sensors, for example using image sensors 260. In some examples, obtaining the images may comprise capturing the images. Some examples of image data may include: one or more images; one or more portions of one or more images; sequence of images; one or more video clips; one or more portions of one or more video clips; one or more video streams; one or more portions of one or more video streams; one or more 3D images; one or more portions of one or more 3D images; sequence of 3D images; one or more 3D video clips; one or more portions of one or more 3D video clips; one or more 3D video streams; one or more portions of one or more 3D video streams; one or more 360 images; one or more portions of one or more 360 images; sequence of 360 images; one or more 360 video clips; one or more portions of one or more 360 video clips; one or more 360 video streams; one or more portions of one or more 360 video streams; information based, at least in part, on any of the above; any combination of the above; and so forth.

In some examples, obtaining image data captured from a construction site (Step 610) may comprise, in addition or alternatively to obtaining image data and/or other input data, obtaining motion information captured using one or more motion sensors, for example using motion sensors 270. Examples of such motion information may include: indications related to motion of objects; measurements related to the velocity of objects; measurements related to the acceleration of objects; indications related to motion of motion sensor 270; measurements related to the velocity of motion sensor 270; measurements related to the acceleration of motion sensor 270; information based, at least in part, on any of the above; any combination of the above; and so forth.

In some examples, obtaining image data captured from a construction site (Step 610) may comprise, in addition or alternatively to obtaining image data and/or other input data, obtaining position information captured using one or more positioning sensors, for example using positioning sensors 275. Examples of such position information may include: indications related to the position of positioning sensors 275; indications related to changes in the position of positioning sensors 275; measurements related to the position of positioning sensors 275; indications related to the orientation of positioning sensors 275; indications related to changes in the orientation of positioning sensors 275; measurements related to the orientation of positioning sensors 275; measurements related to changes in the orientation of positioning sensors 275; information based, at least in part, on any of the above; any combination of the above; and so forth.

In some embodiments, obtaining image data captured from a construction site (Step 610) may comprise receiving input data using one or more communication devices, such as communication modules 230, internal communication modules 440, external communication modules 450, and so forth. Examples of such input data may include: input data captured using one or more sensors; image data captured using image sensors, for example using image sensors 260; motion information captured using motion sensors, for example using motion sensors 270; position information captured using positioning sensors, for example using positioning sensors 275; and so forth.

In some embodiments, obtaining image data captured from a construction site (Step 610) may comprise reading input data from memory units, such as memory units 210, shared memory modules 410, and so forth. Examples of such input data may include: input data captured using one or more sensors; image data captured using image sensors, for example using image sensors 260; motion information captured using motion sensors, for example using motion sensors 270; position information captured using positioning sensors, for example using positioning sensors 275; and so forth.

In some embodiments, analyzing image data, for example by Step 620 and/or Step 630, may comprise analyzing the image data to obtain a preprocessed image data, and subsequently analyzing the image data and/or the preprocessed image data to obtain the desired outcome. One of ordinary skill in the art will recognize that the followings are examples, and that the image data may be preprocessed using other kinds of preprocessing methods. In some examples, the image data may be preprocessed by transforming the image data using a transformation function to obtain a transformed image data, and the preprocessed image data may comprise the transformed image data. For example, the transformed image data may comprise one or more convolutions of the image data. For example, the transformation function may comprise one or more image filters, such as low-pass filters, high-pass filters, band-pass filters, all-pass filters, and so forth. In some examples, the transformation function may comprise a nonlinear function. In some examples, the image data may be preprocessed by smoothing the image data, for example using Gaussian convolution, using a median filter, and so forth. In some examples, the image data may be preprocessed to obtain a different representation of the image data. For example, the preprocessed image data may comprise: a representation of at least part of the image data in a frequency domain; a Discrete Fourier Transform of at least part of the image data; a Discrete Wavelet Transform of at least part of the image data; a time/frequency representation of at least part of the image data; a representation of at least part of the image data in a lower dimension; a lossy representation of at least part of the image data; a lossless representation of at least part of the image data; a time ordered series of any of the above; any combination of the above; and so forth. In some examples, the image data may be preprocessed to extract edges, and the preprocessed image data may comprise information based on and/or related to the extracted edges. In some examples, the image data may be preprocessed to extract image features from the image data. Some examples of such image features may comprise information based on and/or related to: edges; corners; blobs; ridges; Scale Invariant Feature Transform (SIFT) features; temporal features; and so forth.

In some embodiments, analyzing image data, for example by Step 620 and/or Step 630, may comprise analyzing the image data and/or the preprocessed image data using one or more rules, one or more functions and/or procedures, one or more neural networks, one or more object detection algorithms, one or more face detection algorithms, one or more visual event detection algorithms, one or more action detection algorithms, one or more motion detection algorithms, one or more background subtraction algorithms, one or more inference models, and so forth. Some examples of such inference models may include: an inference model preprogrammed manually; a classification model; a regression model; a result of training algorithms, such as machine learning algorithms and/or deep learning algorithms, on training examples, where the training examples may include examples of data instances, and in some cases, a data instance may be labeled with a corresponding desired label and/or result; and so forth.

In some embodiments, analyzing the image data to identify regions depicting concrete (Step 620) may comprise analyzing image data and/or preprocessed image data (such as image data obtained by Step 610) to identify a region of the image data depicting concrete. In some examples, an identified region of the image data may comprise rectangular region of the image data containing a depiction of concrete, map of pixels of the image data containing a depiction of concrete, a single pixel of the image data within a depiction of concrete, a continuous segment of the image data including a depiction of concrete, a non-continuous segment of the image data including a depiction of concrete, and so forth. In some examples, the image data may be preprocessed to identify colors and/or textures within the image data, and a rule for detecting concrete based on the identified colors and/or texture may be used. For example, local histograms of colors and/or textures may be assembled, and concrete may be detected when the assembled histograms meet predefined criterions. In some examples, the image data may be processed with an inference model to detect regions of concrete. For example, the inference model may be a result of a machine learning and/or deep learning algorithm trained on training examples. A training example may comprise example images together with markings of regions depicting concrete in the images. The machine learning and/or deep learning algorithms may be trained using the training examples to identify images depicting concrete, to identify the regions within the images that depict concrete, and so forth. In some examples, the image data may be processed using object detection algorithms to identify objects made of concrete. Some examples of such object detection algorithms may include: appearance based object detection algorithms, gradient based object detection algorithms, gray scale object detection algorithms, color based object detection algorithms, histogram based object detection algorithms, feature based object detection algorithms, machine learning based object detection algorithms, neural networks based object detection algorithms, 2D object detection algorithms, 3D object detection algorithms, still image based object detection algorithms, video based object detection algorithms, and so forth.

In some examples, analyzing the image data to identify regions depicting concrete (Step 620) may further comprise analyzing the image data to determine at least one property related to the detected concrete, such as a size of the surface made of concrete, a color of the concrete surface, a position of the concrete surface (for example based on the position information and/or motion information obtained by Step 610), a type of the concrete surface, and so forth. For example, a histogram of the pixel colors and/or gray scale values of the identified regions of concrete may be generated. In another example, the size in pixels of the identified regions of concrete may be calculated. In yet another example, the image data may be analyzed to identify a type of the concrete surface, such as a wall, a ceiling, a floor, a stair, and so forth. For example, the image data and/or the identified region of the image data may be analyzed using an inference model configured to determine the type of surface. The inference model may be a result of a machine learning and/or deep learning algorithm trained on training examples. A training example may comprise example images and/or image regions together with a label describing the type of concrete surface. The inference model may be applied to new images and/or image regions to determine the type of the surface.

In some embodiments, analyzing the image data to determine quality indications associated with concrete (Step 630) may comprise analyzing image data and/or preprocessed image to determine quality indications associated with the concrete depicted in image data captured using Step 610 and/or in regions identified using Step 620. In some examples, the quality indications may comprise a discrete grade, a continuous grade, a pass/no pass grade, a degree, a measure, a comparison, and so forth. In some examples, the quality indications may comprises an indication of the durability of the concrete, an indication of the strength of the concrete, an estimate of a result of a compressive strength test (for example, of a compressive strength test conducted after a selected curing time, such as 28 days, 30 days, 56 days, 60 days, one month, two months, etc.), an estimate of a result of a water permeability test, an estimate of a result of a rapid chloride ion penetration test, an estimate of a result of a water absorption test, an estimate of a result of an initial surface absorption test, an indication of the condition of the concrete, an indication of segregation of the concrete, an indication of discoloration of the concrete, an indication of scaling of the concrete, an indication of crazing of the concrete, an indication of cracking of the concrete, an indication of curling of the concrete, and so forth.

In some embodiments, Step 630 may process the image data using an inference model to determine quality indications associated with concrete. For example, the inference model may be a result of a machine learning and/or deep learning algorithm trained on training examples. A training example may comprise example images and/or image regions depicting concrete together with desired quality indications. The machine learning and/or deep learning algorithms may be trained using the training examples to generate an inference model that automatically produced quality indications from images of concrete. In some examples, the training examples may comprise images of concrete together with a measure of the durability of the concrete and/or a measure of the strength of the concrete (for example as determined by a test conducted on the concrete after the image was captured, as determined by a test conducted on a sample of the concrete, as determined by an expert, etc.), and the machine learning and/or deep learning algorithms may be trained using the training examples to generate an inference model that automatically produce a measure of the durability of the concrete and/or a measure of the strength of the concrete from images of concrete. In some examples, the training examples may comprise images of concrete together with a result of a test conducted on the concrete after the image was captured or on a sample of the concrete (such as compressive strength test, water permeability test, rapid chloride ion penetration test, water absorption test, initial surface absorption test, etc.), and the machine learning and/or deep learning algorithms may be trained using the training examples to generate an inference model that automatically estimate the result of the test from images of concrete. The above tests may be performed after a selected curing time of the concrete, such as a day, 36 hours, a week, 28 days, a month, 60 days, less than 30 days, less than 60 days, less than 90 days, more than 28 days, more than 56 days, more than 84 days, any combinations of the above, and so forth. In some examples, the training examples may comprise images of concrete together with a label indicating a condition of the concrete (such as ordinary condition, segregation of the concrete, discoloration of the concrete, scaling of the concrete, crazing of the concrete, cracking of the concrete, curling of the concrete, etc.), the machine learning and/or deep learning algorithms may be trained using the training examples to generate an inference model that automatically identify the condition of concrete from images of concrete, and the quality indications may comprise the automatically identified condition of the concrete and/or information based on the automatically identified condition of the concrete.

In some embodiments, Step 630 may process the image data using heuristic rules to determine quality indications associate with concrete. In some examples, histograms based on the image data and/or regions of the image data may be generated. For example, such histograms may comprise histograms of pixel colors, of gray scale values, of image gradients, of image edges, of image corners, of low level image features, and so forth. Further, heuristic rules may be used to analyze the histograms and determine quality indications associate with concrete. For example, a heuristic rule may specify thresholds for different bins of the histogram, and the heuristic rule may determine the quality indications associate with concrete based on a comparison of the histogram bin values with the corresponding thresholds, for example by counting the number of bin values that exceed the corresponding threshold. In some examples, the above thresholds may be selected based on the type of concrete surface (for example as determined by Step 620), for example using one set of threshold values for walls, a second set of threshold values for ceilings, a third set of threshold values for stairs, and so forth.

In some embodiments, Step 620 may identify a plurality of regions depicting concrete in the image data obtained by Step 610. For each identified region, Step 630 may determine quality indications for the concrete depicted in the region. The quality indications of the different regions may be compared, and information may be presented to a user based on the result of the comparison, for example as described below. For example, Step 610 may obtain an image of a staircase made of concrete, Step 620 may identify a region for each stair, Step 630 may assign quality measure for the concrete of each stair, the stair corresponding to the lowest quality measure may be identified, and the identified lowest quality measure may be presented to the user, for example as an overlay next to the region of the stair in the image. In another example, Step 610 may obtain a 360 degrees image of a room made of concrete, Step 620 may identify a region for each wall, Step 630 may assign quality measure for the concrete of each wall, the wall corresponding to the lowest quality measure may be identified, and the identified lowest quality measure may be presented to the user, for example as an overlay on the region of the wall in the image. In yet another example, Step 610 may obtain video depicting concrete pillars, Step 620 may identify a frame and/or a region for each pillar, Step 630 may assign quality measure for the concrete of each pillar, a selected number of pillars corresponding to the highest quality measures may be identified, and the identified highest quality measures and/or corresponding pillars may be presented to the user.

In some embodiments, Step 620 may identify a region depicting concrete in the image data obtained by Step 610, and Step 630 may determine quality indications for the concrete depicted in the region. The quality indications may be compared with selected thresholds, and information may be presented to a user based on the result of the comparison, for example as described below. In some examples, the above thresholds may be selected based on the type of concrete surface (for example as determined by Step 620), for example using one thresholds for wall, a second threshold for ceilings, a third threshold for stairs, and so forth. For example, a quality indication may comprise a measure of the durability of the concrete and/or a measure of the strength of the concrete, the quality indication may be compared with a threshold corresponding to a minimal durability requirement and/or a minimal strength requirement, and an indication may be provided to the user when the measure of durability and/or the measure of strength does not meet the minimal requirement. In another example, a quality indication may comprise an estimated result of a test (such as compressive strength test, water permeability test, rapid chloride ion penetration test, water absorption test, initial surface absorption test, etc.), the quality indication may be compared with a threshold corresponding to minimal requirement (for example according to a standard or regulation), and an indication may be provided to the user when the estimated result of the test does not meet the minimal requirement.

In some embodiments, one or more feedbacks may be provided to one or more users, for example based on the quality indications determined by Step 630. In some examples, feedback may be provided when a quality indication fails to meet some selected criterions, when a quality indication do meet some selected criterions, and so forth. In some examples, the nature and/or content of the feedback may depend on the quality indication and/or the region of the image corresponding to the quality indications. In some examples, the feedbacks may be provided as a: visual output, audio output, tactile output, any combination of the above, and so forth. In some examples, the amount of feedbacks, the events triggering feedbacks, the content of the feedbacks, the nature of the feedbacks, etc., may be controlled by configuration. The feedbacks may be provided: by the apparatus detecting the events, through another apparatus, and so forth.

Figure 7:
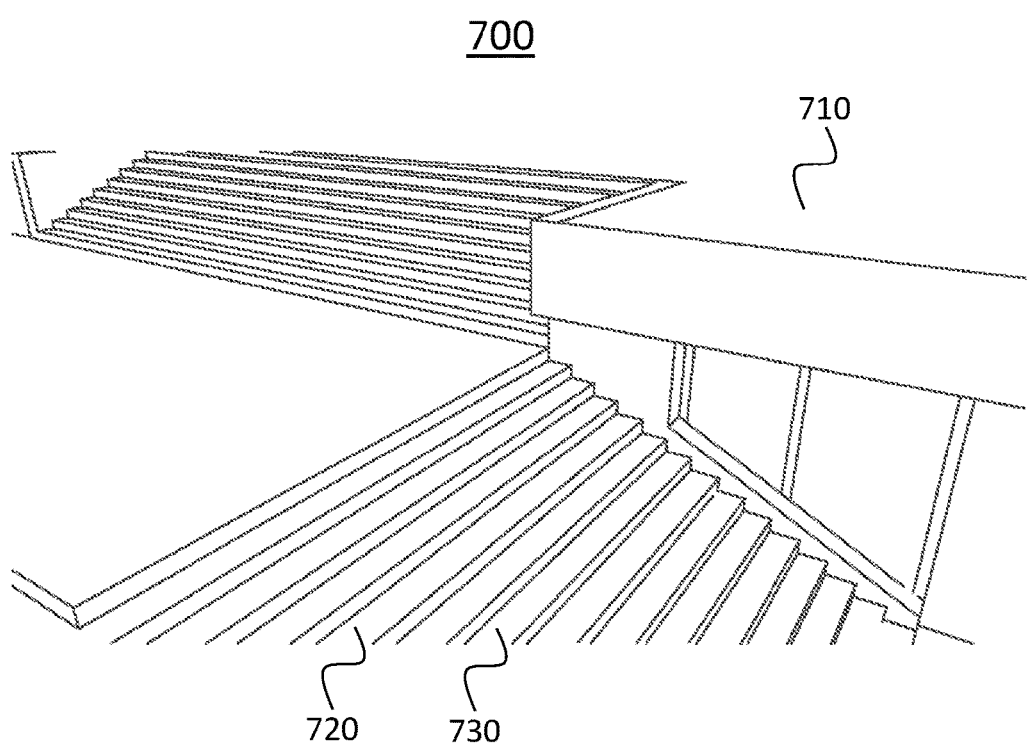
FIG. 7 is a schematic illustration of an example image captured by an apparatus consistent with an embodiment of the present disclosure.

FIG. 7 is a schematic illustration of example image 700 captured by an apparatus, such as apparatus 200. Image 700 may comprise some objects made of concrete, such as surface 710, stair 720 and stair 730. Process 600 may obtain image 700 using Step 610. As described above, Step 620 may identify regions of image 700 corresponding to concrete surface 710, concrete stair 720 and concrete stair 730. As described above, Step 630 may determine quality indications associated with concrete surface 710, concrete stair 720 and concrete stair 730. Information may be provided to a user based on the identified regions and/or determined quality indications. For example, image 700 may be presented to a user with an overlay specifying the identified regions and/or determined quality indications. In addition or alternatively to the presentation of image 700, a textual report specifying the identified regions and/or determined quality indications may be provided to the user.

It will also be understood that the system according to the invention may be a suitably programmed computer, the computer including at least a processing unit and a memory unit. For example, the computer program can be loaded onto the memory unit and can be executed by the processing unit. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A system comprising:
   at least one image sensor configured to capture image data from a construction site; and
   at least one processor configured to:
   analyze the image data to identify a first region and a second region of the image data depicting concrete;
   analyze the image data to determine a first quality indication associated with the concrete depicted in the first region and a second quality indication associated with the concrete depicted in the second region;
   analyze the image data to determine that the first region depicts concrete stairs and that the second region depicts concrete ceilings;
   based on the determination that the first region depicts concrete stairs, compare the first quality indication with a first threshold;
   based on the determination that the second region depicts concrete ceilings, compare the second quality indication with a second threshold, where the second threshold differs from the first threshold;
   based on a result of the comparison of the first quality indication with the first threshold, provide a first indication to a user; and
   based on a result of the comparison of the second quality indication with the second threshold, provide a second indication to the user.

2. The system of claim 1, wherein at least one of the first quality indication and the second quality indication comprises an indication of a durability of the concrete.

3. The system of claim 1, wherein at least one of the first quality indication and the second quality indication comprises an indication of a strength of the concrete.

4. The system of claim 1, wherein the at least one processor is further configured to:
   analyze the image data to identify a condition of the concrete, where the condition of the concrete comprises at least one of segregation of the concrete, discoloration of the concrete, scaling of the concrete, crazing of the concrete, cracking of the concrete, and curling of the concrete; and
   base the determination of at least one of the first quality indication and the second quality indication on the identified condition of the concrete.

5. The system of claim 1, wherein at least one of the first quality indication and the second quality indication comprises an estimate of a result of at least one of a compressive strength test, a water permeability test, a rapid chloride ion penetration test, a water absorption test, and an initial surface absorption test.

6. The system of claim 1, wherein the at least one processor is further configured to:
   analyze the image data to identify a third region of the image data depicting concrete;
   analyze the image data to determine a third quality indication associated with the concrete depicted in the third region;
   analyze the image data to determine that the third region depicts concrete wall;
   based on the determination that the third region depicts concrete wall, compare the third quality indication with a third threshold, where the third threshold differs from the first threshold and the second threshold; and
   based on a result of the comparison of the third quality indication with the third threshold, provide a third indication to the user.

7. The system of claim 1, wherein the at least one processor is further configured to:
   analyze the image data to identify a third region of the image data depicting a first concrete wall and a fourth region of the image data depicting a second concrete wall;
   analyze the image data to determine a third quality indication associated with the first concrete wall depicted in the third region and a fourth quality indication associated with the second concrete wall depicted in the fourth region;
   compare the third quality indication and the fourth quality indication; and
   provide a third indication to the user based on the comparison of the third quality indication and the fourth quality indication.

8. The system of claim 7, wherein the at least one processor is further configured to:
   use the comparison of the third quality indication and the fourth quality indication to select a wall of the first concrete wall and the second concrete wall that corresponds to a lower quality indication; and
   present an image with an overlay associated with a depiction of the selected waft.

9. A method comprising:
   obtaining image data captured from a construction site using at least one image sensor;
   analyzing the image data to identify a first region and a second region of the image data depicting concrete;
   analyzing the image data to determine a first quality indication associated with the concrete depicted in the first region and a second quality indication associated with the concrete depicted in the second region;
   analyzing the image data to determine that the first region depicts concrete stairs and that the second region depicts concrete ceilings;
   based on the determination that the first region depicts concrete stairs, comparing the first quality indication with a first threshold;
   based on the determination that the second region depicts concrete ceilings, comparing the second quality indication with a second threshold, where the second threshold differs from the first threshold;
   based on a result of the comparison of the first quality indication with the first threshold, providing a first indication to a user; and
   based on a result of the comparison of the second quality indication with the second threshold, providing a second indication to the user.

10. The method of claim 9, wherein at least one of the first quality indication and the second quality indication comprises an indication of a durability of the concrete.

11. The method of claim 9, wherein at least one of the first quality indication and the second quality indication comprises an indication of a strength of the concrete.

12. The method of claim 9, further comprising:
  analyzing the image data to identify a condition of the concrete, where the condition of the concrete comprises at least one of segregation of the concrete, discoloration of the concrete, scaling of the concrete, crazing of the concrete, cracking of the concrete, and curling of the concrete; and
  basing the determination of at least one of the first quality indication and the second quality indication on the identified condition of the concrete.

13. The method of claim 9, wherein at least one of the first quality indication and the second quality indication comprises an estimate of a result of a compressive strength test conducted after a selected curing time.

14. The method of claim 9, wherein at least one of the first quality indication and the second quality indication comprises an estimate of a result of a water permeability test.

15. The method of claim 9, wherein at least one of the first quality indication and the second quality indication comprises an estimate of a result of a rapid chloride ion penetration test.

16. The method of claim 9, wherein at least one of the first quality indication and the second quality indication comprises an estimate of a result of at least one of a water absorption test and an initial surface absorption test.

17. The method of claim 9, further comprising:
  analyzing the image data to identify a third region of the image data depicting concrete;
  analyzing the image data to determine a third quality indication associated with the concrete depicted in the third region;
  analyzing the image data to determine that the third region depicts concrete wall;
  based on the determination that the third region depicts concrete wall, comparing the third quality indication with a third threshold, where the third threshold differs from the first threshold and the second threshold; and
  based on a result of the comparison of the third quality indication with the third threshold, providing a third indication to the user.

18. The method of claim 9, further comprising:
  analyzing the image data to identify a third region of the image data depicting a first concrete wall and a fourth region of the image data depicting a second concrete wall;
  analyzing the image data to determine a third quality indication associated with the first concrete wall depicted in the third region and a fourth quality indication associated with the second concrete wall depicted in the fourth region;
  comparing the third quality indication and the fourth quality indication; and
  providing an indication to the user based on the comparison of the third quality indication and the fourth quality indication.

19. The method of claim 18, further comprising:
  use the comparison of the third quality indication and the fourth quality indication to select a wall of the first concrete wall and the second concrete wall that corresponds to a lower quality indication; and
  present an image with an overlay associated with a depiction of the selected wall.

20. A non-transitory computer readable medium storing data and computer implementable instructions for carrying out a method, the method comprising:
  obtaining image data captured from a construction site using at least one image sensor;
  analyzing the image data to identify a first region and a second region of the image data depicting concrete;
  analyzing the image data to determine a first quality indication associated with the concrete depicted in the first region and a second quality indication associated with the concrete depicted in the second region;
  analyzing the image data to determine that the first region depicts concrete stairs and that the second region depicts concrete ceilings;
  based on the determination that the first region depicts concrete stairs, comparing the first quality indication with a first threshold;
  based on the determination that the second region depicts concrete ceilings, comparing the second quality indication with a second threshold, where the second threshold differs from the first threshold;
  based on a result of the comparison of the first quality indication with the first threshold, providing a first indication to a user; and
  based on a result of the comparison of the second quality indication with the second threshold, providing a second indication to the user.

* * * * *